(12) United States Patent

Schuch et al.

(10) Patent No.: US 8,754,253 B2
(45) Date of Patent: Jun. 17, 2014

(54) PROCESS TO OBTAIN A MIXTURE OF LOWER CARBOXYLIC MONO, DI AND TRIESTERS FROM RAW GLYCERIN

(75) Inventors: Cristina Maria Schuch, Campinas (BR); Aires Lacovone, São Paulo (BR)

(73) Assignee: Rhodia Poliamida e Especialidades Ltda, Sao Paulo (BR)

( * ) Notice: Subject to any disclaimer, the term of this patent is extended or adjusted under 35 U.S.C. 154(b) by 220 days.

(21) Appl. No.: 13/382,050

(22) PCT Filed: Jun. 29, 2010

(86) PCT No.: PCT/IB2010/001576
§ 371 (c)(1),
(2), (4) Date: Mar. 23, 2012

(87) PCT Pub. No.: WO2011/001249
PCT Pub. Date: Jan. 6, 2011

(65) Prior Publication Data
US 2012/0178960 A1    Jul. 12, 2012

(30) Foreign Application Priority Data
Jul. 1, 2009  (EP) ..................... 09164316

(51) Int. Cl.
*C07C 67/02*   (2006.01)
(52) U.S. Cl.
USPC ........................................ 560/263
(58) Field of Classification Search
CPC ....................................... C07C 67/08
See application file for complete search history.

(56) References Cited

U.S. PATENT DOCUMENTS

| 2,005,371 | A |   | 6/1935 | Hull |
| 2,173,124 | A |   | 9/1939 | Meyer et al. |
| 4,007,218 | A | * | 2/1977 | Ghanayem et al. ............. 560/99 |
| 4,381,407 | A |   | 4/1983 | Bremus et al. |

FOREIGN PATENT DOCUMENTS

| EP | 1 331 260 A2 | 7/2003 |
| GB | 835 458 | 5/1960 |
| GB | 2 212 493 A | 7/1989 |

OTHER PUBLICATIONS

*International Search Report (PCT/ISA/210) issued on Aug. 25, 2010, by European Patent Office as the International Searching Authority for International Application No. PCT/IB2010/001576.
Schuette et al., "Some Physical Constants of Monacetin, Monopropin and Mono-Normal-Butyrin" Jr. of the Am. Chem. Soc., 1930, pp. 1978-1981, vol. 52, No. 5, American Chemical Society, WDC.
Wessendorf, "Glycerinderivate ALS Kraftstoffkomponenten", Erdoel Erdgas Kohle, 1995, pp. 138-143, vol. 48, No. 3, Urban Verlag, Hamburg, DE.
Galan et al., "From residual to useful oil: Revalorization of glycerin from the biodiesel synthesis", Bioresource Technology, 2009, pp. 3775-3778, vol. 100.

* cited by examiner

*Primary Examiner* — Paul A Zucker
(74) *Attorney, Agent, or Firm* — Dentons US LLP

(57) ABSTRACT

An process to obtain a mixture of lower carboxylic acid mono, di and triesters, from raw glycerin, a by-product of the process to obtain biodiesel, a transesterification of vegetable raw material with lower alcohols is described. Also described is a process to obtain triacetin or a mixture of mono-, di- and triacetin from that raw glycerin, without prior purification.

19 Claims, No Drawings

PROCESS TO OBTAIN A MIXTURE OF LOWER CARBOXYLIC MONO, DI AND TRIESTERS FROM RAW GLYCERIN

This application claims priority under 35 U.S.C. §119 of EP 09164316.3, filed Jul. 1, 2009, and is the United States national phase of PCT/IB2010/001576, filed Jun. 29, 2010, and designating the United States (published in the English language on Jan. 6, 2011, as WO 2011/001249 A1; the title and abstract were also published in English), each hereby expressly incorporated by reference in its entirety and each assigned to the assignee hereof.

The present invention concerns an optimized process to obtain a mixture of lower carboxylic acid mono-, di- and triesters, from raw glycerin, a by-product of the process to obtain biodiesel, a transesterification of vegetable raw material with lower alcohols. The invention particularly refers to an optimized process to obtain triacetin or a mixture of mono, di and triacetin from raw glycerin issued from the transesterifications process to obtain biodiesel, without prior purification.

THE PRIOR ART

Vegetable oil and fat have use as combustibles in general, for diesel cycle engines. The mere replacement of petrol diesel by vegetable oil or fat generates problems in the spray nozzle due, among other reasons, to high viscosity, incomplete combustion, muddy sediments and engine clogging. Those problems can be avoided or lessened through the mixture of vegetable oils to petrol diesel, by the thermal cracking of vegetable oils, by microemulsions of fat acids in petrol diesel using co-solvents, and by the transesterification of animal- or vegetable-origin lipids with lower alcohols.

The transesterification process is method most often employed to enable the use of vegetable oils and animal fat as fuel. From the transesterification reaction in a basic or acid medium, one obtains a monoalkyd ester—the biodiesel—and glycerin. The monoalkyd ester and the glycerin formed in the transesterification reaction are not miscible and are separated by decantation at the end of the reaction.

This raw glycerin, byproduct of the transesterification reaction, has low purity and can contain, among several contaminants, products such as fatty acids, fatty acid salts, inorganic salts, inorganic acids, inorganic bases, water, lower alcohols, mono, di and triglycerides, esters of fatty acids with lower alcohols, and/or transesterification catalyst residue, etc. Raw glycerin typically comprises from 60 to 90% by weight of glycerin, preferably from 60 to 85%, preferably from 80 to 85%. To enable the use of this raw glycerin, the traditional path is the removal of its contaminants by way of several purification steps, to obtain a purer product commonly referred to as blond glycerin, which is the bi-distilled, to reach high purity.

The glycerin thus distilled is then used in the production of derivatives, such as acetates, butyrates and propionates, for a wide spectrum of applications.

Such processes for the previous purification of raw glycerin, aiming to its use in obtaining chemical derivatives, raise its cost and make it less competitive compared to the usual sources for that product.

In the search for alternative, one seeks the use of raw glycerin, unpurified, for the catalytic production of esters.

There are several technical problems to overcome in this direct use alternative, with no previous purification of the raw glycerin from the biodiesel process. For instance, related to the esterification process:

- interference of soaps in the effectiveness of the acid catalysis, as they neutralize the acid esterification catalysts;
- the presence of water and lower alcohols, which tends to alter the reaction balance in the opposite direction;
- the insolubilization of the impurities, which cause incrustations if they are not properly solubilized to be eliminated;
- soluble impurities that hinder the purification process by distillation, retaining the desired esters in the residue;
- the presence of salts that, depending on their nature, raise the risk of corrosion.

The solutions found in the prior art are not effective.

The U.S. Pat. No. 4,381,407 discloses a continuing process for the production of triacetin from glycerin, in a multiple region column, such that the glycerin and the triacetin resulting from the reaction flow in one direction while the acetic acid and water flow in counter current, until a certain yield of triacetin is reached, while acetic anhydride (in the same equipment or in another column) is injected to transform the water in acetic acid, as well as transform mono and diacetin in triacetin. There is no provision in this process for the use of raw glycerin, whose impurities would affect or even impede the realization of the process as described.

The article "*From residual to useful oil: revalorization of glycerin from the biodiesel synthesis*", in Bioresource Technology, available only as an abstract on the internet as from Mar. 6, 2009 (www.ncbi.nlm.nih.gov/pubmed/19269813), mentions that one had determined the reaction kinetics of the triacetin reaction synthesis using glycerin ex-biodiesel process, in a batch reaction, in a reactor under low pressure, in excess of acetic acid. There is no mention to the contaminants present in the glycerin obtained as by-product of the biodiesel process, or how to avoid their harmful effects related to obtaining the triacetins.

This invention seeks to minimize or eliminate the problems and omissions found in the prior art. The process of the invention, briefly, provides in an optimized form a mixture of lower carboxylic acid esters, independently of the quality of the glycerin, the amount and variety of contaminants, such that the mixture as obtains, when the components are added, corresponds to about 98%. An important aspect is the insolubilization of contaminants and its withdrawal in an appropriate moment, particularly by filtration, so as not to harm the continuation of the process. Furthermore, the lower alcohol and the water contained in the raw glycerin are removed from the reaction mass along with the esterification water by way of a continuous azeotropic distillation along the reaction. Due to the presence of water that inhibits the esterification, the lower alcohol, contaminant of the glycerin, leaves the reaction medium without going through significant esterification, being eliminated from the system due to the partition coefficient between the water and the azeotropic agent utilized.

In this way, the present invention concerns an optimized process of obtaining a mixture of mono, di and triesters of lower carboxylic acids from raw glycerin, characterized by the fact that it comprises the following steps:

a. In a reactor comprising a rectification column provided with a condenser and a phase separator for liquids, charge raw glycerin, lower carboxylic acid and/or its anhydride, one or more azeotropic agents, and one or more esterification catalysts;

b. Heat up until total reflux;

c. Rectify and condense vapors, separating the formed organic and aqueous phases;

d. Return the organic phase to the top of the columns, withdrawing the aqueous phase;

e. Perform steps c and d for an adequate period of time;

f. Neutralize the reaction medium at this point or later, in step j;
g. Remove solids at this point or later, in step k, by filtration, decantation or any other adequate manner;
h. Remove the azeotropic agent;
i. Remove the remaining lower carboxylic acid;
j. Neutralize the reaction medium, if item f was not previously performed;
k. Remove solids, if item g was not previously performed;
l. Optionally re-esterify the obtained product, aiming to increase the content of di- and tri-glycerides;
m. Optionally, distill the obtained mixture of esters; provided that the step of removing solids is always performed after a step of neutralization.

In the process of the invention, the neutralization step can be performed before or after the removal of the azeotropic agent and the residual lower carboxylic acid.

In a particular embodiment of the invention, the process aims at obtaining a mixture of the acetate, butyrate and propionate mono-, di- and triesters, respectively from acetic (RN: 64-19-7), propionic (RN: 79-09-4) and butyric (RN: 107-92-6) acids. Advantageously, not imposing any limitation to the invention, the claimed process is turned to obtaining a mixture of monoacetin (1-propanetriol monoacetate, RN: 106-61-6), diacetin (1,3-propanetriol diacetate RN: 25395-31-7) and triacetin (1,2,3-propanetriol triacetate, RN: 102-76-1).

Several considerations about the steps described above are presented, according to particular embodiments of the process of the invention. For ease of description only, one will refer to the context of the reaction between raw glycerin with acetic acid, which is a proper lower carboxylic acid according to the invention, to obtain a mixture of acetins—and that should not be taken as imposing any limitation other than the content of the claims presented further on.

Equipment

Adequate to the process of the invention are reactors with or without mechanical agitation (as ebullition may properly replace mechanical agitation), equipped with rectification columns with two or more theoretical plates.

Lower Carboxylic Acids

Lower carboxylic acids, or their anhydrides, are typically C1-C6, preferably C2-C4 carboxylic acids or anhydrides thereof, for example chosen among acetic, propionic, n-butanoic and iso-butanoic. Also particularly the invention aims at obtaining a mixture of acetins with the use of acetic acid or anhydride. In a particular embodiment of the invention, the purity of the carboxylic acid or anhydride is above 98%.

The excess acid, contaminated with water and azeotropic agent, as well as the acetic acid recovered with acetic anhydride, may be recycled to the process, complementing the amount used in the process with reagents of high purity.

Azeotropic Agents

Heterogeneous azeotropic agents are particularly employed in the process of the invention, i.e., the ones that are immiscible with water but capable of forming with it binary azeotropic mixtures (the water that is either formed during esterification, or present in the reagents). Particularly adequate are the azeotropic agents that carry water with lower contamination of the lower carboxylic acids, with the use of rectification columns. Useful azeotropic agents, without excluding any others, are acetates, butyrates and propionates of lower alcohols, such as ethanol, isopropanol and n-butanol.

If the removal of the azeotropic agent and the residual carboxylic acid is performed after the neutralization, without prior removal of formed precipitated solids, the precipitated mass acquires a compact form that adheres to the equipment, impeding later filtration. If the removal of the azeotropic agent and residual carboxylic acid is performed after the neutralization, the precipitate as formed does not agglomerate in that compact form, and can be effectively removed, for instance by filtration.

The removal of the azeotropic agent is typically performed by fractioned distillation, with low reflux ratio, at atmospheric pressure, providing for the joint distillation of the azeotropic agent and part of the residual acetic acid. The remainder of the acetic acid now withdrawn at atmospheric pressure is removed at reduced pressure.

Catalysts

Useful esterification catalysts, according to the invention, but not excluding any other, are chosen from inorganic acids, such as sulfuric and hydrochloric, and sulfonic, such as methanesulfonic, xylenesulfonic and p-toluene sulfonic. It is understood in the sense employed herein that, in the reaction with glycerin, an amount in excess of carboxylic acid has the effect of displacing the reaction towards the formation of esters, independently of the use of any esterification catalyst. The combined alkalinity of the employed glycerin is an important data for calculating the necessary amount of catalyst, as it corresponds to salts of strong acids with weak bases, able to neutralize the strong acids used as catalysts.

Thus, as mineral or sulfonic acid is used as catalyst, it is advantageous to use such an amount as to remain free acid to act as catalyst. The exceeding amount of acid to use can be calculated from the combined alkalinity, that corresponds to the amount of base which is combined with the fatty acid.

Amounts and Proportions of Reagents

An adequate amount of acetic acid is the stoichiometric one with respect to the amount of glycerin, based on the mass of raw glycerin considered as 100% glycerin.

An adequate amount of acetic acid of an optional further esterification of the reaction mass obtained in the first esterification, after removal of the azeotropic agent and residual acetic acid, is determined as a function of the useful capacity of the equipment to use.

An adequate amount of 100% catalyst corresponds to 0.5 to 0.6% mol w.r.t. the mass of raw glycerin considered as 100% glycerin.

The amount of azeotropic agent is adequately the one necessary to form an azeotrope taking into account the hold-up in the equipment, that is, the amount of azeotropic agent remaining in the decanter, in the pipes and all other trapping points of the equipment.

Period of Time for the Reaction

A period of time in step e of the process to keep the reflux of the reaction medium is any one desired allowing achieving the desired conversion rate and/or the desired respective quantities of mono-, di- and triesters, such as mono-, di- and triacetin. For instance this period of time can be as much as to take the reaction to a content of at least 50% by weight, preferably at least 60%, preferably at least 75%, for example from 75 to 85%, for example 80%, of triesters, for example triacetin, with reference to the total esters obtainable in the reaction. Some further information is provided in the section "MIXTURES OF ESTERS". In some embodiments the period of time can be as much as to take the reaction to a content of from 40% to 70% of monoester, for example monoacetin, with reference to the total esters obtainable in the reaction.

The conversion rate (glycerin converted to esters, disappeared glycerin divided by initial glycerin) can be for example of at least 75% by weight, preferably of at least 90%, preferably of at least 95%, for example as much as 99% or even 100%.

Neutralization

The neutralization of the esterification catalyst aims to insolubilize the contaminants present in the raw glycerin and in the catalyst, as well as to interrupt the reaction and to avoid undesired odors in the final mixture obtained in the process of the reaction.

For instance, when a mixture of acetins is distilled in the presence of a free sulfonic acid, an odor may be present which is undesirable for certain applications, e.g., a raw triacetin distilled in the present of methanesulfonic acid produces a distillate with a garlic-like odor. If the sulfonic acid used as catalyst is neutralized and filtered before distilling the mixture of acetins, or triacetin, a substantially odorless distillate is obtained.

In a particular embodiment, mineral and sulfonic acids used as catalysts are neutralized with carboxylic acid salts, such as sodium or calcium acetates. For example, when calculating the amount of acid catalyst to add, one should consider the combined alkalinity present in the raw glycerin, so as to allow a remaining amount of free catalyst. When acid catalysts are neutralized with calcium bases or salts, there happens the formation of the corresponding calcium salts, for instance calcium xylenesulfonate, calcium p-toluenesulfonate or calcium sulfate, which are of difficult filtration, making necessary the use filtration adjuvants, to avoid the clogging of the filter. Calcium methanesulfonic acid does not present this inconvenience, being easier to filter.

Raw glycerin, a by-product of biodiesel process, containing sulfates, generates at the end of the present process of esterification a calcium sulfate precipitate which, depending on its amount, may influence in the filterability of the generated residue in the neutralization step of the esterification product.

It is usual to employ sodium methylate as a catalyst in the biodiesel process. If, in that process, this base is neutralized with excess mineral acid, such an excess will contaminate the raw glycerin that is decanted to be separated from the biodiesel. This excess should preferably be taken into account in the steps of adding catalyst and neutralization of the process of this invention.

In the process to obtain biodiesel, the neutralization of the transesterification product with hydrochloric acid gives origin to a sodium chloride contamination solubilized the decanted glycerin. The presence of sodium chloride may cause accelerated corrosion in stainless steel equipment. According to the invention, when one performs the esterification of glycerin with acetic acid in the absence of acid catalyst, there happens the formation a precipitate rich in sodium chloride, easy to remove by filtration as a consequence of a lower content of glycerin in the esterification medium.

When the catalyst in the reaction medium is not neutralized before the removal of the azeotropic agent and the residual acetic acid, the present of active catalyst in a distillation operation has as consequence the advancement of the reaction to a higher level compared to when the catalyst is neutralized.

Removal of Whatever is not Ester from the Reaction Medium

The removal of residual carboxylic acid, after the fractioned distillation of the azeotropic agent along with part of the same residual carboxylic acid, is typically performed under reduced pressure in a further low reflux ratio fractioned distillation.

The removal of solids generated by the insolubilization of most contaminants contained in the glycerin can be performed by any proper means, for instance decantation or filtration. Without any limitation, adequate filters are of the sparkler or bag types.

Sometimes the distillate has a residual acetic acid odor that can be eliminated by steam distillation.

When methanesulfonic acid is used as catalyst, and its neutralization is performed with calcium acetate, a precipitate of calcium methanesulfonate is obtained which can easily be eliminated by filtration without clogging problems in the filtering medium.

Mixture of Esters

In particular, in the process of obtaining a mixtures of mono-, di- and triesters, such as a mixture of mono-, di- and triacetin according to the invention, azeotropic agents such as acetates of lower alcohols like ethanol, isopropanol and butanol are advantageously employed. Those acetates, in the presence of an acid catalyst and acetic acid react partially with glycerin, mono- and diacetin to produce monoacetin, di- and triacetin, respectively, liberating the lower alcohol b the transesterification process. The liberated lower alcohol reacts with acetic acid present in the reaction mass to partially regenerate the original acetate, due to the low content of water in the reaction mass.

When a mixture of mono-, di- and triesters of a specific carboxylic acid is aimed at, such as acetic acid to obtain acetins, it is particularly advantageous to use as azeotropic agent one or more acetates of lower alcohols—as well as it is advantageous to use propionates as azeotropic agents to obtain propionins, and butyrates to obtain butyrins. That avoids the formation of a mixture of mixed esters, as it is the case, for instance, when the esterification reaction of raw glycerin is performed with acetic acid and the azeotropic agent is a butyrate, what favors the formation of a mixture of acetins and butyrins, rather than a mixture of only acetins.

The mixture of mono-, di- and triacetins, obtained according to the invention from glycerin ex-biodiesel, is adequate to give continuation to the esterification, aiming to higher content of di- and triesters, or even only triesters. In that sense, within a particular embodiment of the invention, after obtaining a mixture of esters according to the steps described hereinbefore, the process can be repeated, using as raw material this very mixture instead of raw glycerin. The result is the transformation of mono- into diesters and di- into triesters.

In the mixture the respective quantities of mono-, di- and triesters, such as a mixture of mono-, di- and triacetin can vary. These quantities can be determined by the use of the product. Appropriate quantities are known be the one skilled in the art. For example in tanning industry mixtures with higher amounts of monoesters such as monoacetin are preferred.

In one embodiment the mixture has at least 50% by weight, preferably at least 60%, preferably at least 75%, for example from 75 to 85%, for example 80%, of triesters, for example triacetin, with reference to the total esters obtainable in the reaction.

In one embodiment, useful for example in foundry industry, the mixture has at least 80% by weigh of triesters, such as triacetate.

In one embodiment the mixture has less than 10% by weight of monoester such as monoacetin.

In one embodiment the mixture has 40 to 70% by weight of monoester such as monoacetin.

The mixture of esters can be used as a solvent, for example as a solvent used in foundry or as a solvent for basic dyes. It can also be used as a fuel additive. It can also be used as a plasticizer, a softening agent, an agent for tanning leather, a fixative in perfumery, a topical antifungal, a solvent for antifungal agents used in agricultural or pharmaceuticals formulations.

EXAMPLES

The following is a series of examples of particular embodiments of the invention, which do not impose limitations to the invention, other than what is described in the claims attached to this document.

Example 1

472 g raw glycerin, by-product of biodiesel process, with approximate composition described in table I, was mixed with 909 g acetic acid, 90 g butyl acetate and 4 g of a 70% aqueous solution methanesulfonic acid, heated up until total reflux. The vapors leaving the reaction mass were rectified in a column with 3 theoretical plates, condensed, and the organic and aqueous phase were continuously separated by decantation. The organic phase was returned to the top of the column and the aqueous phase was discarded. The operation lasted about 5 h, the reaction mass temperature varying within 110-130° C. and 80-90° C. at the top of the column. The reaction mass was neutralized with 30 g acetic acid, 10 g water and 4 g calcium carbonate. The neutralized reaction mass was filtered and the filtrate was subject to a flash distillation to remove the butyl acetate and the residual acetic acid, such that the butyl acetate was distilled at atmospheric pressure, with temperatures of the reaction mass within 120-150° C., and 90-100° C. at the top of the column. Then residual acetic acid was removed by distillation at 200-50 mm Hg, with reaction mass temperature within 90-120° C. and 50-30° C. at the top of the column. After removal of butyl acetate and residual acetic acid, temperature from 130 to 150° C. and 90 to 125° C. at the top of the column. The distilled mixture of actins presented the characteristics shown in table II.

TABLE I

Characteristics of raw glycerin, biodiesel by-product.

| | |
|---|---|
| Combined alkalinity (meq/g) | 1.62 |
| Acidity (mg KOH/g) | 1.06 |
| Volatiles at 100° C. | 1.39 |
| Ester content (%) | 12.95 |
| Glycerin content (%) | 83.72 |

TABLE II

Characteristics of distilled mixture of acetins

| | |
|---|---|
| Water (%) | 0.08 |
| Acidity (mg KOH/g) | 0.32 |
| Monoacetin (%) | 1.21 |
| Diacetin (%) | 19.62 |
| Triacetin (%) | 77.48 |

Comments—example 1 shows that the process works with high ester content glycerin, butyl acetate as azeotropic agent and methanesulfonic acid as catalyst in the presence of combined alkalinity. It also shows that the precipitated impurities are filterable, after neutralization, and before the recovery of butyl acetate and acetic acid.

Example 2

472 g raw glycerin, by-product of the biodiesel process, with approximate composition shown in table III, containing 2.17 g free sulfuric acid as revealed by its strong acidity, was mixed with 909 g acetic acid, 90 g butyl acetate and 0.7 g 98% sulfuric acid, and heated up until total reflux. The vapors leaving the reaction mass were rectified in a column with 3 theoretical plates, condensed, and the organic and aqueous phases were continuously separated by decantation. The organic phase returned to the top of the column and the aqueous phase discarded. The operation lasted about 5 hours, the reaction mass temperature varying from 110 to 130° C., and 80 to 90° C. at the top of the column.

The non-neutralized reaction mass, presenting a proportion among acetins as shown in table IV, was subject to flash distillation to remove the butyl acetate and the residual acetic acid. The butyl acetate was distilled at atmospheric pressure, with reaction mass temperature within 120-150° C. and 90-100° C. at the top of the column. The acetic acid was removed by reduced pressure distillation at 200-500 mm Hg, the reaction mass temperature within 90-120° C. and 50-30° C. at the top of the column. After recovery of the butyl acetate and the residual acetic acid, the proportion of the acetins reached new values as shown in table IV.

TABLE III

Characteristics of the raw glycerin, biodiesel by-product.

| | |
|---|---|
| Combined alkalinity (meq/g) | <0.01 |
| Strong acidity (mg KOH/g) | 5.26 |
| Week acidity (mg KOH/g) | 3.44 |
| Total acidity (mg KOH/g) | 8.70 |
| Volatiles at 100° C. (% w/w) | 9.37 |
| Ester content (% w/w) | 9.21 |
| Glycerin content (% w/w) | 81.08 |

TABLE IV

Content of acetins in mixture

| Acetin | Before the distillation of butyl acetate/acetic acid (weight %) | After the distillation of butyl acetate/acetic acid (weight %) |
|---|---|---|
| Monoacetin | 9.62 | 7.10 |
| Diacetin | 54.72 | 50.50 |
| Triacetin | 35.65 | 42.36 |

Comments—example 2 shows that the process works with high volatile content glycerin, and that the high free mineral acidity in the form of sulfuric acid acts as catalyst. It also shows that the reaction continues during the recovery of both the azeotropic agent and the residual acetic acid.

Example 3

476 raw glycerin, biodiesel by-product, with approximate composition shown in table V, was mixed with 910 g acetic acid, 90 g isopropyl acetate and heated up until total reflux. The vapors leaving the reaction mixture were rectified in a column with 6 theoretical plates, condensed and the organic and aqueous phases continuously separated. The organic phase returned to the top of the column, and the aqueous phase discarded. The operation lasted about 11 hours, the reaction mass temperature varying between 110 and 130° C., and 68-71° C. at the top of the column. The reaction mass presenting a proportion of acetins shown in table VI was subject to flash distillation to remove the isopropyl acetate and the residual acetic acid. The isopropyl acetate was distilled under atmospheric pressure, the reaction mass temperature varying from 140 to 150° C., and 80 to 100° C. at the top of the column. The residual acetic acid was distilled under 200-50 mm Hg reduced pressure, the reaction mass temperature varying from 75 to 140° C. and 40 to 45° C. at the top of the column. A total of 427.4 g of a mixture were recovered, containing 81.6% acetic acid, 13.8% isopropyl acetate and 4.5% water. After recovery of isopropyl acetate and residual acetic acid, the proportion among the acetins reached new values, as shown on table VI. After recovery of isopropyl acetate and residual acetic acid, the mixture of acetins was filtered, the filtrand (residue) is dried in a stove, producing a mass of 33.8 g with 86.46% sodium chloride. To the filtrate, it was added the 427.4 g of the acetic acid/isopropyl acetate previously recovered, 31.9 g isopropyl acetate, 561.5 g acetic acid and 4.3 g 70% methane sulfonic acid aqueous solution of, and heated up to total reflux. The vapors leaving the reaction mass were rectified in a column with 6 theoretical plates, condensed and the organic and aqueous phases continuously separated. The organic phase returned to the top of the column and the aqueous phase was discarded. This operation lasted about 7 hours, the reaction mass temperature varying from 115 to 127° C., and 70 to 74° C. at the top of the column. The reaction mass presenting the proportion of acetins shown in table VI was subject to a flash distillation to withdraw the isopropyl acetate and the residual acetic acid. The isopropyl acetate was distilled at atmospheric pressure, with reaction mass temperature varying from 120 to 140° C., and 75 C to 106° C. at the top of the column. The residual acetic acid was distilled at 200-50 mm Hg reduced pressure, the reaction mass temperature varying from 100 to 150° C. and 40 to 30° C. at the top of the column. The remaining reaction mass was the neutralized with a mixture of 30 g acetic acid, 10 g water and 4 g calcium carbonate, filtered and distilled at 4-6 mm Hg reduced pressure, the reaction mass temperature varying from 140 to 160° C., and 130 to 135° C. at the top of the column. The distilled acetin mixture presented the characteristics shown in table VI.

TABLE V

Characteristics of raw glycerin, biodiesel by-product.

| | |
|---|---|
| Combined alkalinity (meq/g) | 0.03 |
| Strong acidity (mg KOH/g) | 0.02 |
| Total acidity (mg KOH/g) | 0.09 |
| pH (10% aqueous solution) | 4.3 |
| Water (% w/w) | 11.9 |
| NaCl (% w/w) | 6.6 |
| Glycerin content (% w/w) | 80.02 |

TABLE VI

Acetin content

| Acetins | Before the distillation of isopropyl acetate/ acetic acid (weight %) without catalyst | After the distillation of isopropyl acetate/ acetic acid (weight %) without catalyst | Before the distillation of isopropyl acetate/ acetic acid (weight %) with catalyst | After the distillation of isopropyl acetate/ acetic acid (weight %) without catalyst | Mixture of acetins, distilled at 4-6 mmHg |
|---|---|---|---|---|---|
| Monoacetin | 8.41 | 9.12 | 0.24 | 0.11 | 0.28 |
| Diacetin | 53.00 | 48.34 | 18.46 | 10.7 | 8.7 |
| Triacetin | 38.58 | 42.53 | 81.29 | 89.2 | 91.0 |

Comments—example 3 shows that the process works with glycerin containing high level of sodium chloride, and that this salt can be insolubilized by way of the esterification with acetic acid in the absence of catalyst to minimize the corrosive effect of sodium chloride; and that the presence of a catalyst promotes a higher conversion of reagents into products. It also shows that isopropyl acetate works as azeotropic agent, that high content of water in the glycerin do significantly not interfere in the process, that the recovered azeotropic agent and acetic acid can be recycled in the process without prior purification, and that the precipitated impurities are filterable after recovery of the azeotropic agent/acetic acid, before neutralization.

Example 4

472 g raw glycerin, biodiesel by-product, with approximate composition shown in table VII, was mixed with 909 g acetic acid, 90 g butyl acetate, and 4 g 70% methanesulfonic acid aqueous solution, and heated up until total reflux. The vapors leaving the reaction mass were rectified in a column with 3 theoretical plates, condensed, and the organic and aqueous phases continuously separated. The organic phase returned to the top of the column and the aqueous phase discarded. This operation lasted about 8 hours, the reaction mass temperature varying from 110 to 130° C., and 80 to 83° C. at the top of the column. The reaction mass was neutralized with a mixture of 30 g acetic acid, 10 g water and 4 g calcium carbonate, and then filtrated. The filtrated was subject to a flash distillation to remove butyl acetate and residual acetic acid. The butyl acetate and the residual acetic acid was distilled at a pressure of 600-100 mm Hg, the reaction mass temperature varying from 125 to 126° C., and 90 to 52° C. at the top of the column. After the recovery of butyl acetate and residual acetic acid, 306 g acetic anhydride was added to the mixture of obtained acetins, and let react for 2 h at 150-160° C. The acetic acid generated by the reaction with the acetic anhydride, and the excess acetic anhydride were distilled at a pressure of 600-50 mm Hg, with the reaction mass temperature varying within 70-120° C., and 90-40° C. at the top of the column. The raw triacetin thus obtained was distilled at 2-5 mm Hg reduced pressure, the mass reaction temperature varying from 100 to 110° C., and 110 to 125° C. at the top of the column. The distilled triacetin was subject to steam distillation by adding 200 g along 2 h, under a pressure of 100 mm Hg, the base temperature varying from 100 to 110° C., and 45 to 50° C. at the top. The characteristics of the obtained triacetin are shown in table VIII.

TABLE VII

Characteristics of raw glycerin, biodiesel by-product.

| | |
|---|---|
| Combined alkalinity (meq/g) | 1.62 |
| Acidity (mg KOH/g) | 1.06 |
| Volatiles at 100° C. | 1.39 |

TABLE VII-continued

| Characteristics of raw glycerin, biodiesel by-product. | |
| --- | --- |
| Ester content % | 12.95 |
| Glycerin content % | 83.72 |

TABLE VIII

| Characteristics of the obtained triacetin | |
| --- | --- |
| Density (g/ml) | 1.160 |
| Refraction index | 1.4135 |
| Water content % | 0.42 |
| Triacetin contend % | 99.25 |
| Acidity (mg KOH/g) | 0.94 |

Comments—example 4 shows that from a high ester content glycerin, using butyl acetate as azeotropic agent, methanesulfonic acid as catalyst, in the presence of combined alkalinity and complementing the reaction with acetic anhydride, it is possible to obtain a food grade triacetin.

Example 5

473.2 g raw glycerin, biodiesel by-product, with approximate composition as shown on Table V, was mixed with 911.8 g acetic acid, 90.9 g ethyl acetate, 4.4 g 70% methanesulfonic acid aqueous solution, was heated up to total reflux. The vapors leaving the reaction mass were rectified in a column with 3 theoretical plates, condensed, and the organic and aqueous phases continuously separated. The organic phase returned to the top of the column, and the aqueous phase was discarded. This operation lasted about 20 hours, the reaction mass temperature varying from 108 to 168° C., and 62 to 66° C. at the top of the column. The reaction mass presenting the proportion among the acetins as shown on table IX was subject to a flash distillation to remove the ethyl acetate and the residual acetic acid. The ethyl acetate was distilled at atmospheric pressure, the reaction mass temperature varying from 168 to 178° C. and 62 to 55° C. at the top of the column. The residual acetic acid was distilled at 60 mm Hg reduced pressure, the reaction mass temperature varying from 129 to 160° C. and 35 to 34° C. at the top of the column. After recovery of ethyl acetate and residual acetic acid, the proportion of acetins reached new values also shown on table IX. After recovery of ethyl acetate and residual acetic acid, the acetin mixture was filtrated.

TABLE IX

| | Acetin content | |
| --- | --- | --- |
| Acetin | Before distillation of ethyl acetate/acetic acid (weight %) | After distillation of ethyl acetate/acetic acid (weight %) |
| Monoacetin | 0.82 | 0.17 |
| Diacetin | 23.16 | 15.13 |
| Triacetin | 76.00 | 84.70 |

Comments—Example 5 shows that from the same glycerin as in example 3, employing ethyl acetate as azeotropic agent, it is possible to obtain high conversion in triacetin, in only one esterification step if water removal from the reaction is proportional to its generation, what means the maintenance of azeotropic distillation for a long period of time.

The information contained in the foregoing, as well as what is contained in the examples, allow a person skilled in the art to perform alternative embodiments, not expressly described, but which employ the function taught herein with the results revealed herein. Such equivalent embodiments are encompassed by the scope of the invention and therefore covered by the claims presented further on.

The invention claimed is:

1. A process of obtaining a mixture of mono, di and triesters comprising at least 60% of triesters of C1-C6 carboxylic adds from raw glycerin obtained from the transesterification process of animal-or-vegetable-origin lipids to obtain biodiesel, without prior purification, comprising from 60% to 90% by weight of glycerin, the process comprising the following steps:
   a. charging a reactor comprising a rectification column provided with a condenser and a phase separator for liquid, with raw glycerin, C1-C6 carboxylic add and/or its anhydride, one or more azeotropic agents, and one or more esterification catalysts;
   b. heating until total reflux;
   c. rectifying and condensing vapors, separating the formed organic and aqueous phase;
   d. returning the organic phase to the top of the column, withdrawing the aqueous phase;
   e. performing steps c and d for a period of time sufficient to take the reaction to a content of 80% of triester with respect to the total esters obtainable by the reaction;
   f. optionally neutralizing the reaction medium at this point;
   g. removing solids at this point or later, in step k;
   h. removing the azeotropic agent;
   i. removing the remaining C1-C6 carboxylic acid;
   j. neutralizing the reaction medium, if the neutralization of step f was not previously performed;
   k. removing solids, if item g was not previously performed;
   l. optionally re-esterifying the product obtained in step k; and
   m. optionally, distilling the obtained mixture of esters;
   wherein the step of removing solids is always performed after a step of neutralization.

2. The process according to claim 1, wherein said C1-C6 carboxylic acid is acetic, propionic or butyric.

3. The process according to claim 1, wherein said C1-C6 carboxylic acid is acetic acid.

4. The process according to claim 1, wherein the esterification catalyst of said C1-C6 carboxylic acid is an inorganic acid, or sulfonic acid.

5. The process according to claim 1, wherein the amount of said C1-C6 carboxylic acid is stoichiometric with respect to the raw glycerin.

6. The process according to claim 1, wherein the amount of catalyst corresponds to 0.5% to 0.6% mol with respect to the raw glycerin.

7. The process according to claim 1, wherein said neutralization step is performed with carboxylic acid salts.

8. The process according to claim 1, wherein said rectification column is provided with at least two theoretical plates.

9. The process according to claim 1, wherein the removal of the solids is performed by filtration or decantation.

10. The process according to claim 9, wherein the filtration is performed with a sparkler or bag type filter.

11. The process according to claim 1, wherein the removal of azeotropic agent is performed at atmospheric pressure distillation.

12. The process according to claim 1, wherein the removal of the residual C1-C6 carboxylic acid is performed at reduced pressure.

13. The process according to claim 1, wherein the azeotropic agent is an acetate, a propionate or a butyrate.

14. The process according to claim 1, wherein said azeotropic agent is an acetate of ethanol, isopropanol or butanol, when the C1-C6 carboxylic acid is acetic acid or anhydride.

15. The process according to claim 1, wherein said azeotropic agent and said residual carboxylic acid, removed from the reaction medium are re-utilized in said process.

16. The process according to claim 3, wherein the carboxylic acid is above 97% purity.

17. The process according to claim 4, wherein when the esterification catalyst is an inorganic acid, the inorganic acid is sulfuric acid or hypochloric acid.

18. The process according to claim 4, wherein when the esterification catalyst is a sulfonic acid, the sulfonic acid is methanesulfonic, xylenesulfonic or p-toluene sulfonic acid.

19. The process according to claim 7, wherein the carboxylic acid slit is a calcium salt or a sodium salt.

\* \* \* \* \*